(12) United States Patent
Yoshida

(10) Patent No.: US 6,643,488 B1
(45) Date of Patent: Nov. 4, 2003

(54) INTERMEDIATE TRANSFER DRUM FOR ELECTRO-PHOTOGRAPHIC PROCESS AND IMAGE FORMING APPARATUS USING THE SAME

(75) Inventor: Minoru Yoshida, Tokyo (JP)

(73) Assignees: Kabushiki Kaisha Toshiba, Tokyo (JP); Toshiba Tec Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/175,359

(22) Filed: Jun. 20, 2002

(51) Int. Cl.[7] ............................................. G03G 15/16
(52) U.S. Cl. ...................................... 399/308; 399/302
(58) Field of Search ................................ 399/297, 302, 399/308

(56) References Cited

U.S. PATENT DOCUMENTS

| | | | |
|---|---|---|---|
| 5,187,526 A | | 2/1993 | Zaretsky |
| 5,666,599 A | | 9/1997 | Miyasaka et al. |
| 5,669,052 A | * | 9/1997 | Kusaba et al. ............... 399/308 |
| 5,732,314 A | * | 3/1998 | Tsukida et al. .............. 399/302 |
| 5,752,130 A | * | 5/1998 | Tanaka et al. ........... 399/308 X |
| 6,009,297 A | * | 12/1999 | Maeda et al. ................ 399/302 |
| 6,097,920 A | * | 8/2000 | Hara et al. ................... 399/302 |

FOREIGN PATENT DOCUMENTS

JP     09-146385     6/1997

OTHER PUBLICATIONS

U.S. patent application Ser. No. 10/046,228, Yoshida, filed Jan. 16, 2002.
U.S. patent application Ser. No. 09/927,388, Yoshida, filed Aug. 13, 2001.

* cited by examiner

Primary Examiner—Sandra Brase
(74) Attorney, Agent, or Firm—Foley & Lardner

(57) ABSTRACT

In an intermediate transfer drum 6, rubber hardness of a rubber belt 62 is set to not more than 80°; assuming that the ratio between outside diameter R (mm) of a base drum 61 and inside diameter r (mm) of the rubber belt 62 is P, and 100% tensile stress of the rubber belt 62 is f1 (kgf/cm$^2$), then f1×(P−1)≧5; and permanent elongation in the actual using state of the rubber belt 62 is set to not more than 10%. According to the intermediate transfer drum 6, in an image formed, there is no phenomenon such that deviation in color occurs, the rubber belt 62 is twisted and levitated, resulting in defective transfer or irregular transfer.

5 Claims, 5 Drawing Sheets

(A)

(B)

INTERMEDIATE TRANSFER DRUM FOR ELECTRO-PHOTOGRAPHIC PROCESS AND IMAGE FORMING APPARATUS USING THE SAME

BACKGROUND OF THE INVENTION

1. Field of the Invention

The present invention relates to an intermediate transfer drum for an electro-photographic process, which is suitably applied to a printing apparatus or an image forming apparatus employing an electro-photographic process such as a laser printer, an electro-photographic copying machine or the like, particularly applied to a color printing apparatus or a color image forming apparatus employing an electro-photographic process, and an image forming apparatus using the same.

2. Related Art Statement

In a color printing apparatus or a color image forming apparatus employing an electro-photographic process, the systems for carrying out putting colors one upon another using a plurality of colors of toner include various systems such as one for carrying out putting colors one upon another on a photosensitive body, one for carrying rout that on a sheet of paper, one for carrying out that on an intermediate transfer body or the like.

In the system for carrying out putting colors one upon another on a photosensitive body out of the above-described systems, since it is necessary to carry out exposing again from the top of a toner image formed on the photosensitive body, the toner image formed already becomes disordered or the like, resulting in a great defect of image quality formed.

On the other hand, in the system for carrying out putting colors one upon another on a sheet of paper, with respect to the system for carrying out putting colors one upon another on an intermediate transfer body, which requires two transfers such that a primary transfer is carried out from the photosensitive body to the intermediate transfer body, and a secondary transfer is carried out from the intermediate transfer body to a sheet of paper, one time transfer will suffice, and therefore, the above-described system has been heretofore used generally, and has been employed for various color copying machines.

On the other hand, the system for carrying out putting colors one upon another on an intermediate transfer body, which has been considered to be disadvantageous in terms of image quality, has been employed for a color printer or the like whose image quality is not so much demanded, in which the intermediate transfer body has a belt shape, and making use of advantages such that the space efficiency within the printing device, or corresponding properties of paper such as cardboard are excellent.

As the forms of the above-described intermediate transfer body, a belt shape, a drum shape or the like are considered, but as the intermediate transfer body of the drum shape (hereinafter referred to as an intermediate transfer drum), generally, use is made of one in which a rubber belt is put on the outer circumferential surface of a metal drum.

In the intermediate transfer drum as described, when a slip occurs between the rubber belt and the metal drum, a deviation of color occurs in an image formed, or the rubber belt becomes twisted and levitates, resulting in defective transfer, and irregular transfer.

Particularly, where there is not equipped with means for driving the intermediate transfer drum, when the photosensitive body is driven, a great load is applied to the surface of the intermediate transfer drum. Further, even where there is equipped with means for driving the intermediate transfer drum at a speed equal to that of the photosensitive body, where there is equipped with a blade cleaning means for cleaning the surface of the intermediate transfer drum, a great load is applied to the surface of the intermediate transfer drum by the contact of the blade therewith. And, due to such a load as described, a slip or deviation becomes occurred between the rubber belt and the metal drum.

From the foregoing, there is generally employed the procedure wherein when the rubber belt is put on the outer circumferential surface of the metal drum, an adhesive is poured into and between the outer circumferential surface of the metal drum and the inner circumferential surface of the rubber belt so as not to generate a slip between the rubber belt and the metal drum.

However, in the procedure as described above, unless the adhesive is uniformly coated, the surface of the intermediate transfer drum becomes rugged so that irregular transfer occurs, because of which the yield of the intermediate transfer drum cannot be enhanced, making it difficult to achieve mass production. Further, when reuse of the metal drum or the rubber belt is taken into consideration, if the metal drum and the rubber belt are bonded together, they cannot be separated easily, greatly impairing the reuse.

SUMMARY OF THE INVENTION

The present invention has been accomplished in view of the conventional a problems noted above with respect to the intermediate transfer drum in which the rubber belt is put on the outer circumferential surface of the metal drum. It is an object of the invention to provide an intermediate transfer drum and an image forming apparatus using the same, in which even if a great load is applied to the surface of the intermediate transfer drum, no slip occurs between the rubber belt and the metal drum, and there occurs no phenomenon such that in an image formed, deviation of color occurs, or the rubber belt becomes twisted and levitated, resulting in defective transfer or irregular transfer.

It is another object of the invention to provide an intermediate transfer drum and an image forming apparatus using the same, in which without employing the procedure for pouring an adhesive into and between the outer circumferential surface of the metal drum and the inner circumferential surface of the rubber belt, the yield of the intermediate transfer drum to enable facilitating mass production, and the metal drum and the rubber belt can be separated easily so as to enable reusing them.

For achieving the aforementioned objects, the intermediate transfer drum according to the present invention is characterized in that assuming that the rubber hardness of the rubber belt is not more than 80°, the ratio between the outside diameter R (mm) of the metal drum and the inside diameter r (mm) of the rubber belt is P. and 100% tensile stress of the rubber belt is f1 (kgf/cm$^2$), then f1×(P−1)±5 results, and the permanent elongation in the actual using state of the rubber belt is set to 10% or less.

DETAILED DESCRIPTION OF THE INVENTION

The preferred embodiment of the intermediate transfer drum according to the present invention will be explained in detail hereinafter with reference to the drawings.

Figure 1:
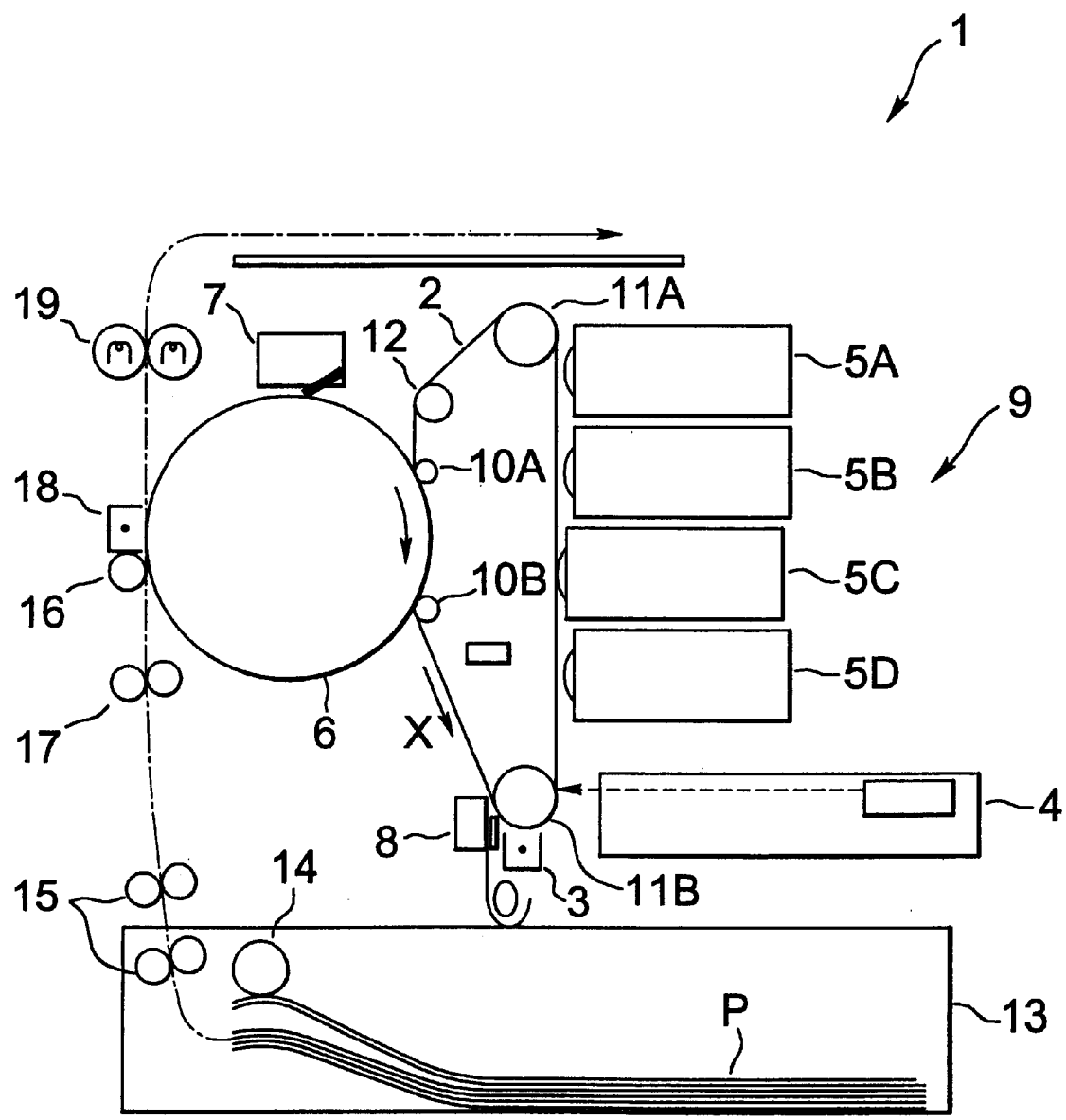
FIG. 1 is a longitudinal sectional view of an image forming apparatus employing a blade system as an intermediate transfer body cleaning device.

First, the image forming apparatus 1 shown in FIG. 1 using the intermediate transfer drum according to the present invention will be explained.

The image forming apparatus 1 has an image forming section 9 comprising a belt-like photosensitive body 2 (hereinafter referred to as a photosensitive belt), a charging device 3 for charging the photosensitive belt 2 to a fixed potential, an exposing device 4 for irradiating light on the charged photosensitive belt 2 to form an electrostatic latent image, first to fourth developing devices 5A, 5B, 5C, and 5D for supplying toner to the electrostatic latent image formed on the photosensitive belt 2 to visualize it, an intermediate transfer drum 6 for carrying and supporting once a toner image formed on the photosensitive belt 2 by the developing devices 5A, 5B, 5C, and 5D, an intermediate transfer body cleaning device 7 for cleaning the intermediate transfer drum 6, and a photosensitive body cleaning device 8 for removing toner remained on the photosensitive belt 2.

The photosensitive belt 2 is applied with a fixed tensile force by first and second press rollers 10A and 10B for placing the outer circumferential surface of the intermediate transfer drum 6 and the surface of the photosensitive belt 2 in close contact, first and second holding rollers 11A and 11B for holding a gap between the developing devices 5A, 5B, 5C, and 5D and the photosensitive belt 2 constant, and a tension regulating roller 12, the above-described rollers being driven and rotated by a drive motor not shown provided in order to drive any of the above-described rollers whereby it is rotated at fixed speed in the direction of X indicated by the arrow.

At the lower part of the image forming apparatus 9, there is disposed a sheet (paper) cassette 13 for storing sheets of paper P as an output material having a fixed size. At one end of the sheet cassette 13, there is disposed a paper feeding roller 14 for taking out the sheets of paper P within the cassette 13 sheet by sheet, and between the sheet cassette 13 and the intermediate transfer drum 6, there is constituted a carrying system 15 for carrying the sheets of paper P in the direction of the intermediate transfer drum 6.

On the upstream side of a transfer roller 16, that is, on the side of the sheet cassette 13, there is disposed an aligning roller 17 for once stopping a sheet of paper P being carried by the carrying system 15, correcting an inclination of the sheet of paper P with respect to the carrying direction, and coinciding an extreme end of the sheet of paper P with an extreme end of a toner image formed on the intermediate transfer drum 6. Further, on the downstream side of the transfer roller 16, there are disposed a peeling device 18 for applying an AC charge in order to peel the sheet of paper P to which a toner image is transferred from the intermediate transfer drum 6, and a fixing device 19 for fixing to the sheet of paper P the toner image transferred to the sheet of paper P by heating and pressurizing.

With the constitution as described above, the sheet of paper P having transferred by the carrying system 15 is put in and supported between the intermediate transfer drum 6 and the transfer roller 16, and the toner image on the intermediate transfer drum 6 is transferred to the sheet of paper P by an electric field produced between the intermediate transfer drum 6 and the transfer roller 16.

Next, the operation for performing a full-color printing using the image forming apparatus 1 shown in FIG. 1 will be explained.

First, the surface of the rotating photosensitive belt 2 is uniformly charged by the charging device 3. Continuously, exposing corresponding to a yellow image is applied to the surface of the photosensitive belt 2 by the exposing device 4 to form an electrostatic latent image. Continuously, the electrostatic latent image formed on the surface of the photosensitive belt 2 is developed with a yellow toner by the developing device 5A for yellow toner, and further, a yellow image is primarily transferred onto the intermediate transfer drum 6.

The above primary transfer is carried out by an electric field created due to a potential difference between a base on the back of the photosensitive belt 2 and a substrate drum of the intermediate transfer drum 6. In the image forming apparatus 1 in accordance with the present embodiment, for example, the base of the photosensitive belt 2 is set to a potential 0V, and a bias voltage of +600 to +1200 V is applied to the substrate drum of the intermediate transfer drum 6 depending upon the installing environment or the using degree of the intermediate transfer drum 6.

After having passed through the transfer area, the photosensitive belt 2 is destaticized with light irradiation by a destaticizing device, the yellow toner remained on the surface of the photosensitive belt 2 without being transferred to the intermediate transfer drum 6 is cleaned by a photosensitive body cleaning device 8, and the yellow toner cleaned is restored into a waste toner box.

Next, the surface of the photosensitive belt 2 is charged again by a charging device 3, and exposing corresponding to a magenta image is carried out by the exposing device 4 to form an electrostatic latent image. Continuously, the electrostatic latent image on the surface of the photosensitive belt 2 is developed with a magenta toner by the developing device 5B for magenta. Then, the magenta image is transferred onto the intermediate transfer drum 6, and is put on the yellow image having been formed already.

Then, a cyan image and a black image are likewise subjected to the process similar to that mentioned above to form a four-color (four colors put one upon another) toner image on the intermediate transfer drum 6.

Thereafter, a sheet of paper P is supplied to and between the intermediate transfer drum 6 and the transfer roller 16, and the four-color (four colors put one upon another) toner image formed on the intermediate transfer drum 6 is collectively secondary-transferred to the sheet of paper P. The sheet of paper P having the four-color (four colors put one upon another) toner image held thereon is peeled from the intermediate transfer drum 6 by the peeling device 18, and in the fixing device 19 the four-color (four colors put one upon another) toner image is fixed, on the surface of which is formed a color image.

On the other hand, since some toner not being transferred to the sheet of paper P remain on the intermediate transfer drum 6, a blade of an intermediate transfer body cleaning device 7 is brought into contact with the intermediate transfer drum 6 after secondary transfer to clean the latter. In the image forming apparatus 1 of the present embodiment, the blade system is employed as the intermediate transfer body cleaning device 7, and the blade pressing force when in contact with the intermediate transfer drum 6 is set to a linear load of 1.7 g/cm.

It is noted that in the process from the formation of the four-color (four colors put one upon another) toner image on the intermediate transfer drum 6 to the secondary transfer thereof to the sheet of paper P, the cleaning blade is separated from the intermediate transfer drum 6.

Further, in the image forming apparatus 1 according to the present embodiment, the photosensitive belt 2 and the intermediate transfer drum 6 are independently driven by stepping motors, respectively, and according to the stepping motors, the circumferential speeds of the photosensitive belt 2 and the intermediate transfer drum 6 can be coincided with each other with high accuracy, and a color image with extremely less color deviation can be formed.

Next, the intermediate transfer drum 6 of the present invention, which is applied to the above-described image forming apparatus 1, will be explained.

Figure 2:
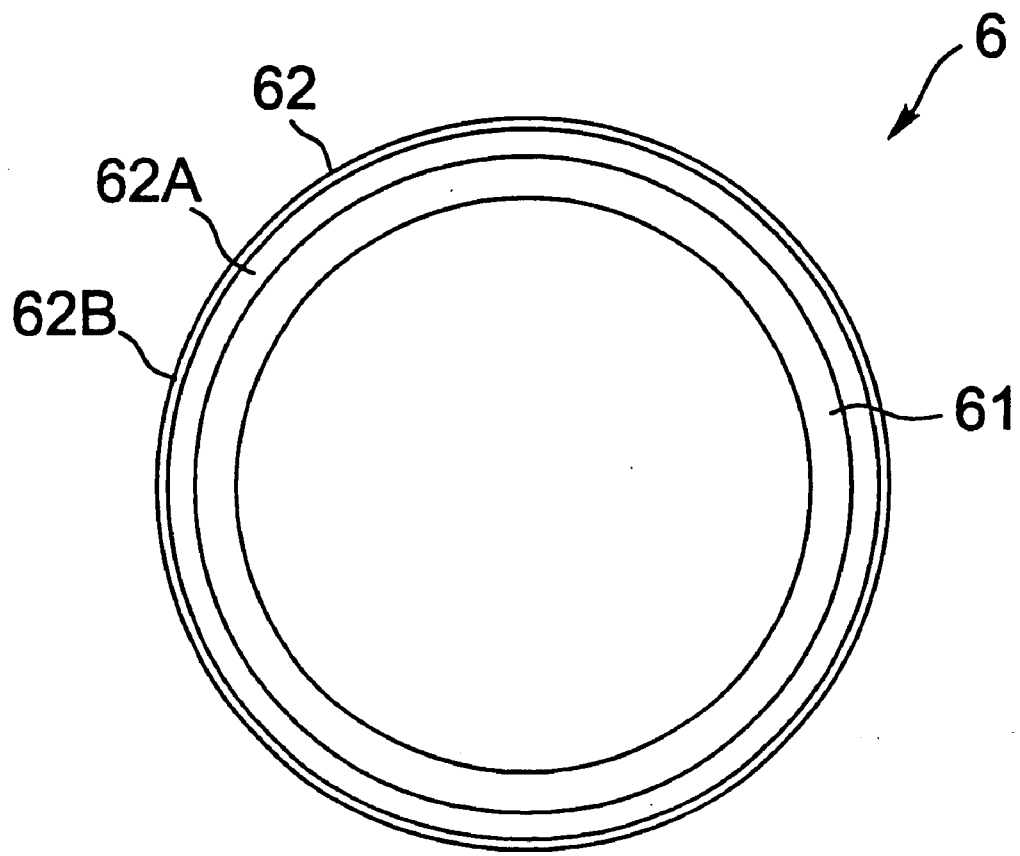
FIG. 2 is a longitudinal sectional view of an intermediate transfer drum according to the present invention.

As shown in FIG. 2, the intermediate transfer drum 6 is constituted by putting a rubber belt 62 of thickness 1.0 mm on a drum 61 made of aluminum of outside diameter 168 mm, and the outside diameter after put is approximately 170 mm. "Approximately 170 mm" termed here is because of that since the rubber belt 62 is put while being extended, the thickness of the rubber belt 62 after put becomes somewhat thin. And, an adhesive layer is not formed between the rubber belt 62 and the drum made of aluminum 61.

The rubber belt 62 is constituted such that fluorine rubber, fluorine resin, nylon coating, urethane coating or the like which are excellent in toner release properties is coated on the surface of a base layer 62A formed of rubber or elastomer such as chloroprene rubber (CR), urethane rubber (UR), nitrile butadiene rubber (NBR), silicone rubber (QR), ethylene propylene copolymer elastomer (EPDM) or the like to form a surface layer 62B. In the present embodiment, 10 μm of fluorine rubber is coated on the surface of the base layer 62A formed of chloroprene rubber to form a surface layer 62B.

Resistance Value of the Intermediate Transfer Drum

Figure 3:
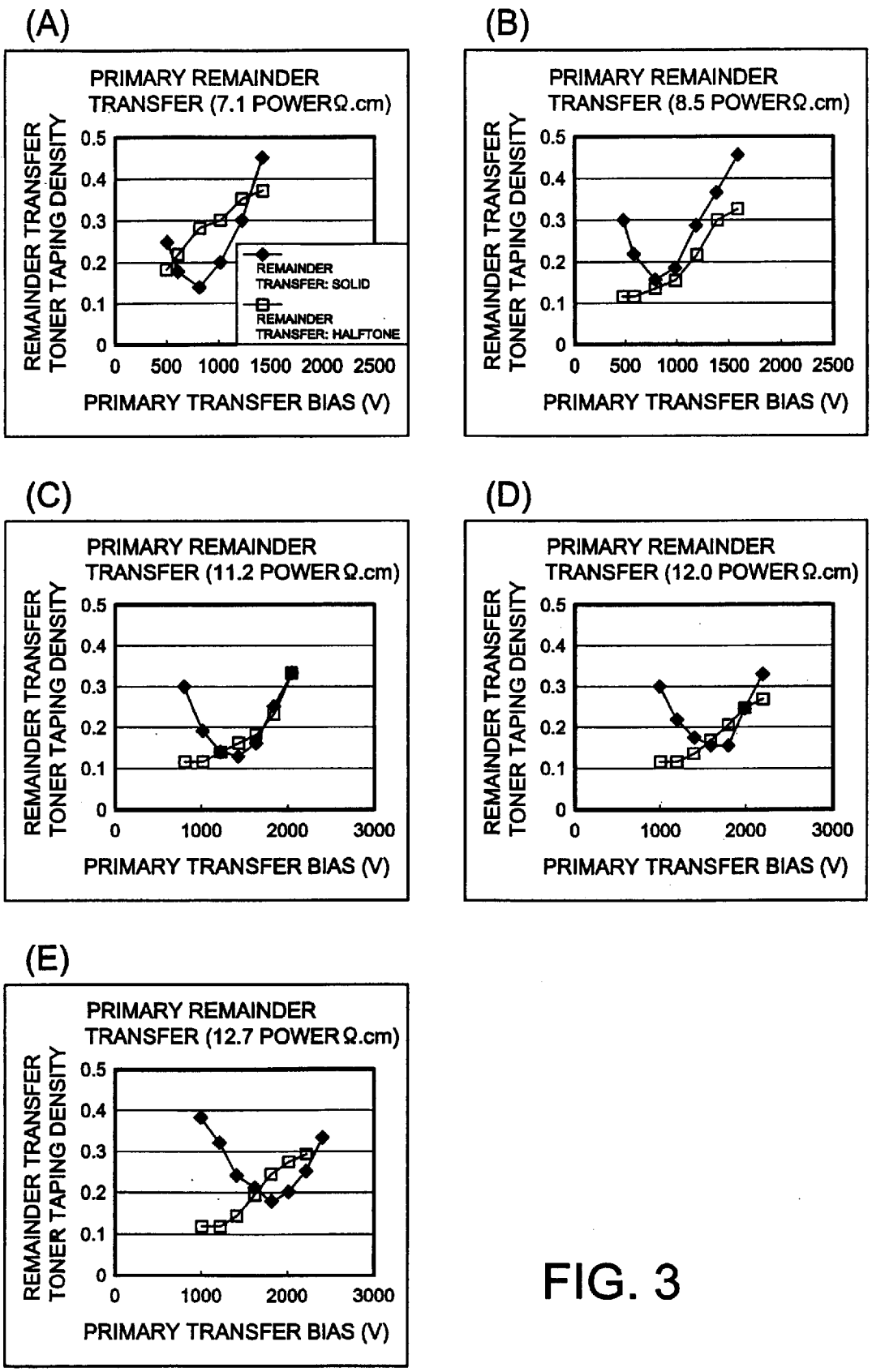
FIG. 3 is a view showing a relationship between an applied bias voltage at the time of a primary transfer and a remaining toner quantity after the primary transfer with respect to an intermediate transfer drum having various resistance values.

FIG. 3 shows a relationship between an applied bias voltage at the time of primary transfer and a remaining toner quantity after primary transfer with respect to the intermediate transfer drum 6 having various resistance values. The resistance values of the intermediate transfer drum 6 were measured, by a resistance measuring device 'Hyrester' made in Mitsubishi Chemical, in case where a voltage of 500V is applied for 30 seconds. Further, development was made by magenta toner, and it was set up so that for a solid portion of a toner image and for a half tone portion, magenta toner of 0.70 mg/cm$^2$ and magenta toner of 0.25 mg/cm$^2$ are respectively adhered. And, toner remained on the photosensitive belt 2 after primary transfer was subjected to taping, which was pasted to a sheet of white paper and was measured by a MacBeth densitometer.

According to FIG. 3, it is understood that if the resistance value of the intermediate transfer drum 6 is within the range of $10^8$ to $10^{12}$ Ω·cm, the proper value of the applied bias voltage is different, but the remaining toner quantities of the solid portion and the half tone portion can be made to be not more than 0.15 with the above-described measured density, and proper transfer can be carried out.

Rubber Hardness of Rubber Belt

TABLE 1 shows the forming state of the line image in case where the rubber hardness (JIS-A) of the rubber belt 62 and the pressing force at the time of the secondary transfer are variously changed. As the transfer roller 16, a urethane sponge roller of hardness 35° (ASKER-C) is used, and with respect to the line image, a line in a sub-scanning direction of width 300 μm, which is said to cause inside-missing to occur extremely easily, is printed, and the line image was evaluated visually.

TABLE 1

| SECONDARY TRANSFER | RUBBER HARDNESS OF RUBBER BELT (°) | | | | | |
|---|---|---|---|---|---|---|
| LOAD (gf/cm) | 50 | 63 | 71 | 80 | 85 | 90 |
| 7 | ⊚ | ⊚ | ⊚ | ⊚ | ○ | x |
| 12 | ⊚ | ⊚ | ⊚ | ⊚ | x | x |
| 20 | ⊚ | ⊚ | ⊚ | ⊚ | x | x |
| 24 | ⊚ | ⊚ | ⊚ | ○ | x | x |
| 30 | ⊚ | ⊚ | ○ | ○ | x | x |

In TABLE 1, ⊚ indicates that the line is positively printed, being extremely good; ○ indicates that there is no inside-missing of the line, being good; and X indicates that there is inside-missing of the line, being bad. It is understood from TABLE 1 that the pressing force at the time of the secondary transfer is changed whereby the rubber hardness of the rubber belt 62 capable of holding the line image in a good state is also changed, but generally, if the rubber hardness of the rubber belt 62 is not more than 80°, the good line image without inside-missing can be formed. Further, it is understood that if the pressing force at the time of the secondary transfer is not more than 20 gf/cm, a better line image can be formed.

Transfer Characteristic of Rubber Belt

In the intermediate transfer drum 6 for putting the rubber belt 62 on the metal drum 61 without adhering, there is a problem that transfer-missing occurs due to looseness of the rubber belt 62. If the rubber belt 62, whose rubber hardness is made as high as possible and tensile stress is made as high as possible, is used while being stretched out, at the beginning close adhesion between the metal drum 61 and the rubber belt 62 is enhanced, and no transfer-missing due to looseness occurs. However, when the rubber belt 62 is used while being extremely stretched out, at the time of use for a long period the rubber belt 62 is gradually extended, and transfer-missing due to looseness occurs.

So, with respect to each of eight kinds (A to H) of the rubber belts 62, in which material compositions and molding conditions of urethane-base rubber belts are variously changed, and which are different in rubber hardness and 100% tensile stress, as shown in TABLE 2, samples whose thickness is 1 mm, and inside diameter is varied from 142 to 166 mm, were prepared, and the situation of occurrence of transfer-missing at the beginning and at the time of use for a long period was examined.

TABLE 2

| | RUBBER HARDNESS OF RUBBER BELT (° :JIS-A) | 100% TENSILE STRESS (kgt/cm$^2$) |
|---|---|---|
| A | 78 | 160 |
| B | 76 | 80 |
| C | 68 | 110 |
| D | 68 | 90 |
| E | 68 | 75 |

TABLE 2-continued

| RUBBER HARDNESS OF RUBBER BELT (° :JIS-A) | 100% TENSILE STRESS (kgt/cm$^2$) |
|---|---|
| F | 62 | 80 |
| G | 62 | 60 |
| H | 58 | 63 |

Transfer Characteristic at the Beginning

The above-described sample of the rubber belt 62 was put on the metal drum 61 of outside diameter 168 mm to constitute the intermediate transfer drum 6, a line in a sub-scanning direction of width 300 μm was printed, and the situation of occurrence of transfer-missing was visually observed. The results are as shown in TABLE 3. Here, ○ indicates that there is no transfer-missing, being good, and X indicates that there is transfer-missing, being bad.

TABLE 3

| | | SAMPLE OF RUBBER BELT | | | | | | | |
|---|---|---|---|---|---|---|---|---|---|
| r (mm) | R/r | A | B | C | D | E | F | G | H |
| 142 | 1.183099 | ○ | ○ | ○ | ○ | ○ | ○ | ○ | ○ |
| 143 | 1.174825 | ○ | ○ | ○ | ○ | ○ | ○ | ○ | ○ |
| 144 | 1.166667 | ○ | ○ | ○ | ○ | ○ | ○ | ○ | ○ |
| 145 | 1.158621 | ○ | ○ | ○ | ○ | ○ | ○ | ○ | ○ |
| 146 | 1.150685 | ○ | ○ | ○ | ○ | ○ | ○ | ○ | ○ |
| 147 | 1.142857 | ○ | ○ | ○ | ○ | ○ | ○ | ○ | ○ |
| 148 | 1.135135 | ○ | ○ | ○ | ○ | ○ | ○ | ○ | ○ |
| 149 | 1.127517 | ○ | ○ | ○ | ○ | ○ | ○ | ○ | ○ |
| 150 | 1.12 | ○ | ○ | ○ | ○ | ○ | ○ | ○ | ○ |
| 151 | 1.112583 | ○ | ○ | ○ | ○ | ○ | ○ | ○ | ○ |
| 152 | 1.105263 | ○ | ○ | ○ | ○ | ○ | ○ | ○ | ○ |
| 153 | 1.098039 | ○ | ○ | ○ | ○ | ○ | ○ | ○ | ○ |
| 154 | 1.090909 | ○ | ○ | ○ | ○ | ○ | ○ | ○ | ○ |
| 155 | 1.083871 | ○ | ○ | ○ | ○ | ○ | ○ | ○ | ○ |
| 156 | 1.076923 | ○ | ○ | ○ | ○ | ○ | ○ | x | x |
| 157 | 1.070064 | ○ | ○ | ○ | ○ | ○ | ○ | x | x |
| 158 | 1.063291 | ○ | ○ | ○ | ○ | x | ○ | x | x |
| 159 | 1.056604 | ○ | x | ○ | ○ | x | x | x | x |
| 160 | 1.05 | ○ | x | ○ | x | x | x | x | x |
| 161 | 1.043478 | ○ | x | x | x | x | x | x | x |
| 162 | 1.037037 | ○ | x | x | x | x | x | x | x |
| 163 | 1.030675 | ○ | x | x | x | x | x | x | x |
| 164 | 1.02439 | x | x | x | x | x | x | x | x |
| 165 | 1.018182 | x | x | x | x | x | x | x | x |
| 166 | 1.012048 | x | x | x | x | x | x | x | x |

It is understood from TABLE 3 that due to materials and properties of the rubber belt 62, the lower limit value of the ratio (R/r) between outside diameter of the metal drum 61 and inside diameter of the rubber belt 62, which occurs no transfer-missing at the beginning, is different, and when the 100% tensile stress (f1) becomes large, the lower limit value of (R/r) at which no transfer-missing occurs becomes small.

So, assuming that the lower limit value of (R/r) at which at the beginning no transfer-missing occurs is α, f1×(α−1) was calculated relative to eight kinds (A to H) of rubber belts 62. The results are shown in TABLE 4. It is understood from TABLE 4 that f1×(α−1) shows the value of about 5 irrespective of materials and properties of the rubber belt 62. therefore, if the value of f1×(R/r−1) is set to 5 or greater, it is possible to prevent transfer-missing at the beginning from occurring.

TABLE 4

| | f1 | LOWER LIMIT VALUE OF (R/r) | f1 × (R/r − 1) |
|---|---|---|---|
| A | 160 | 1.031 | 4.96 |
| B | 80 | 1.063 | 5.04 |
| C | 110 | 1.05 | 5.5 |
| D | 90 | 1.057 | 5.13 |
| E | 75 | 1.07 | 5.25 |
| F | 80 | 1.063 | 5.04 |
| G | 60 | 1.084 | 5.04 |
| H | 63 | 1.084 | 5.292 |

Transfer Characteristic at the Time of Long-period Use

Next, 100,000 sheets in A4 Format of a line in a sub-scanning direction of width 300 μm were printed using the above-described intermediate transfer drum 6 in which no transfer-missing occurred at the beginning. The results of visual observation of the situation of occurrence of transfer-missing after printing of 100,000 sheets were as shown in Table 5. Here, ○ indicates that there is no transfer-missing, being good, and X indicates that there is transfer-missing, being bad.

TABLE 5

| | | SAMPLE OF RUBBER BELT | | | | | | | |
|---|---|---|---|---|---|---|---|---|---|
| r (mm) | R/r | A | B | C | D | E | F | G | H |
| 142 | 1.183099 | x | x | ○ | x | x | x | x | x |
| 143 | 1.174825 | x | x | ○ | x | x | x | x | x |
| 144 | 1.166667 | ○ | x | ○ | x | x | x | x | x |
| 145 | 1.158621 | ○ | ○ | ○ | x | x | x | ○ | x |
| 146 | 1.150685 | ○ | ○ | ○ | x | x | x | ○ | x |
| 147 | 1.142857 | ○ | ○ | ○ | ○ | x | ○ | ○ | x |
| 148 | 1.135135 | ○ | ○ | ○ | ○ | ○ | ○ | ○ | x |
| 149 | 1.127517 | ○ | ○ | ○ | ○ | ○ | ○ | ○ | x |
| 150 | 1.12 | ○ | ○ | ○ | ○ | ○ | ○ | ○ | ○ |
| 151 | 1.112583 | ○ | ○ | ○ | ○ | ○ | ○ | ○ | ○ |
| 152 | 1.105263 | ○ | ○ | ○ | ○ | ○ | ○ | ○ | ○ |
| 153 | 1.098039 | ○ | ○ | ○ | ○ | ○ | ○ | ○ | ○ |
| 154 | 1.090909 | ○ | ○ | ○ | ○ | ○ | ○ | ○ | ○ |
| 155 | 1.083871 | ○ | ○ | ○ | ○ | ○ | ○ | ○ | ○ |
| 156 | 1.076923 | ○ | ○ | ○ | ○ | ○ | ○ | x | x |
| 157 | 1.070064 | ○ | ○ | ○ | ○ | ○ | ○ | x | x |
| 158 | 1.063291 | ○ | ○ | ○ | ○ | x | ○ | x | x |
| 159 | 1.056604 | ○ | x | ○ | ○ | x | x | x | x |
| 160 | 1.05 | ○ | x | ○ | x | x | x | x | x |
| 161 | 1.043478 | ○ | x | x | x | x | x | x | x |
| 162 | 1.037037 | ○ | x | x | x | x | x | x | x |
| 163 | 1.030675 | ○ | x | x | x | x | x | x | x |
| 164 | 1.02439 | x | x | x | x | x | x | x | x |
| 165 | 1.018182 | x | x | x | x | x | x | x | x |
| 166 | 1.012048 | x | x | x | x | x | x | x | x |

According to TABLE 5, when the value of (R/r) becomes great, transfer-missing will occur after printing of 100,000 sheets, but the upper limit value of (R/r) at which no transfer-missing occurs is not always related to large or small values of the belt hardness and 100% tensile stress (f1).

Permanent Elongation of Rubber Belt

Figure 4:
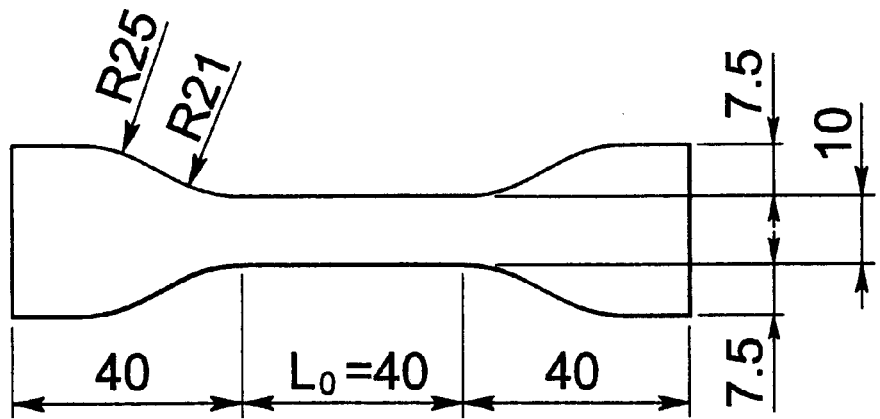
FIG. 4 (A) is a front view of a dumbbell specimen, and FIG. 4 (B) is an explanatory view of a measuring method of a permanent extension.
Figure 4:
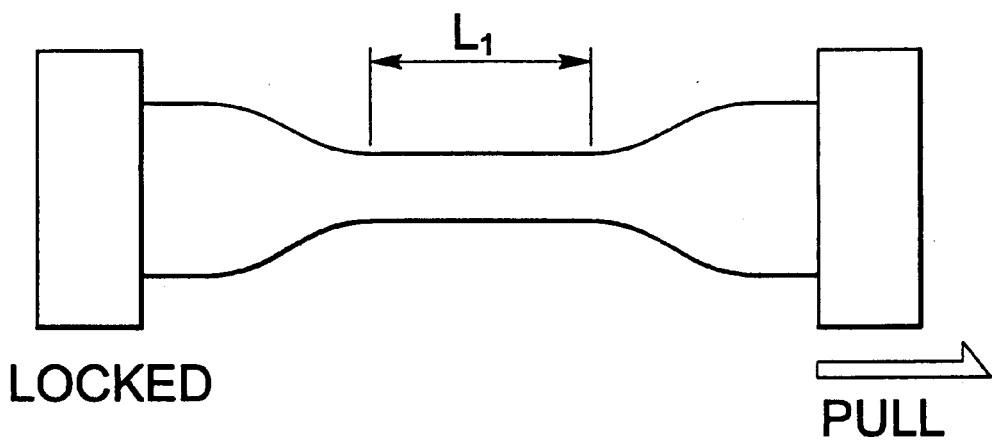

The permanent elongation when the rubber belt 62 is actually used (hereinafter referred to as an actual using state) was measured by a specimen and measuring method as shown in FIG. 4. As the shape of a specimen, the shape of dumbbell specimen No. 1 described in JIS K6301 (Vulcanizate physical test method) was employed as shown in FIG. 4 (A). The method for adding gage marks to a specimen and the method for measuring the distance between gage marks were conformed to JIS K6301.

Assuming that the distance between gage marks L0 in a non-load state is 40 mm, the distance between gage marks in an actual using state is to be extended to (40×R/r) mm. So, the load was applied for 10 minutes in the state that the distance between gage marks of the specimen was extended to (40×R/r) mm, the load was released after passage of 10 minutes, and the distance between gage marks L1 after release was measured.

The permanent elongation β(%) of the rubber belt 62 in the actual using state is defined by the following equation.

$$\beta = (L1-40)/l \times 100$$

wherein $$l = 40(1-R/r)$$

The results of calculation of the permanent elongation β(%) of the rubber belt 62 in the actual using state relative to eight kinds (A to H) of rubber belts 62 are shown in TABLE 6. It is understood from comparison between TABLES 5 and 6 that where the permanent elongation β(%) in the actual using state is not more than 10%, even after use for a long period, such phenomenon that the rubber belt 62 is loosened, resulting in occurrence of transfer-missing will not occur.

Where the brush is placed in contact with the intermediate transfer drum 6, it seems that the rubber belt 62 is not so much waved because the pressing force is small as compared with the case where the blade is placed in contact; however actually, also where the brush is used, transfer-missing due to waving of the rubber belt 62 occurs.

Where the photosensitive belt 2 is removed, and the blade is placed in contact with the intermediate transfer drum 6, and where the brush is placed in contact with the intermediate transfer drum 6, drive torques of the intermediate transfer drum 6 were measured in each case, results of which are shown in TABLE 7. It is understood from Table 7 that the brush is mechanically in contact with the intermediate transfer drum 6 with small pressing force, but when the bias voltage is applied, the brush is adsorbed in the intermediate transfer drum 6 to generate a load about equal to the case of the blade.

TABLE 7

| CLEANING MEMBER | BIAS VOLTAGE | TORQUE (kg · f) |
| --- | --- | --- |
| BLADE | **** | 1.1 |
| BRUSH | OFF | 0.2 |
| BRUSH | ON | 1.2 |

Since inside-missing of the line image depends upon the rubber hardness of the rubber belt 62, if the rubber hardness

TABLE 6

ELONGATION IN ACTUAL USING STATE = (L1 − 40) /l × 100 (%)

| r (mm) | R/r | A | B | C | D | E | F | G | H |
| --- | --- | --- | --- | --- | --- | --- | --- | --- | --- |
| 142 | 1.183099 | 20.808 | 31.404 | 7.5096 | 18.433 | 45.058 | 28.673 | 11.606 | 43.01 |
| 143 | 1.174825 | 12.87 | 17.16 | 7.15 | 17.16 | 40.04 | 26.455 | 11.154 | 37.895 |
| 144 | 1.166667 | 9.75 | 11.25 | 6.3 | 16.05 | 21 | 19.5 | 10.5 | 30.9 |
| 145 | 1.158621 | 5.3587 | 9.7717 | 4.413 | 13.554 | 17.337 | 15.13 | 9.4565 | 24.114 |
| 146 | 1.150685 | 3.4841 | 9.6227 | 2.6545 | 12.443 | 14.102 | 12.277 | 9.2909 | 19.909 |
| 147 | 1.142857 | 2.8 | 9.45 | 2.275 | 9.975 | 11.725 | 9.625 | 9.275 | 16.625 |
| 148 | 1.135135 | 2.775 | 9.805 | 2.22 | 9.62 | 9.99 | 8.14 | 9.805 | 14.245 |
| 149 | 1.127517 | 2.3526 | 10.195 | 1.9605 | 8.6263 | 9.6066 | 3.725 | 8.8224 | 11.567 |
| 150 | 1.12 | 1.6667 | 10.417 | 1.6667 | 8.125 | 8.9583 | 1.6667 | 8.125 | 9.7917 |
| 151 | 1.112583 | 0.6662 | 10.437 | 1.3324 | 7.9941 | 7.10 | 0.6662 | 8.2162 | 9.1044 |
| 152 | 1.105263 | 0.475 | 10.45 | 0.7125 | 8.075 | 5.225 | 0 | 7.6 | 9.2625 |
| 153 | 1.098039 | 0.255 | 8.16 | 0 | 7.395 | 4.08 | 0 | 6.885 | 9.18 |
| 154 | 1.090909 | 0 | 6.875 | 0 | 6.875 | 3.85 | 0 | 6.875 | 8.25 |
| 155 | 1.083871 | 0 | 5.0673 | 0 | 5.3654 | 3.875 | 0 | 6.8558 | 7.75 |
| 156 | 1.076923 | 0 | 4.225 | 0 | 4.55 | 3.9 | 0 | x | x |
| 157 | 1.070064 | 0 | 4.2818 | 0 | 3.5682 | 3. | 0 | x | x |
| 158 | 1.063291 | 0 | 4.345 | 0 | 3.16 | x | 0 | x | x |
| 159 | 1.056604 | 0 | x | 0 | 2.2083 | x | x | x | x |
| 160 | 1.05 | 0 | x | 0 | x | x | x | x | x |
| 161 | 1.043478 | 0 | x | x | x | x | x | x | x |
| 162 | 1.037037 | 0 | x | x | x | x | x | x | x |
| 163 | 1.030675 | 0 | x | x | x | x | x | x | x |
| 164 | 1.02439 | x | x | x | x | x | x | x | x |
| 165 | 1.018182 | x | x | x | x | x | x | x | x |
| 166 | 1.012048 | x | x | x | x | x | x | x | x |

Figure 5:
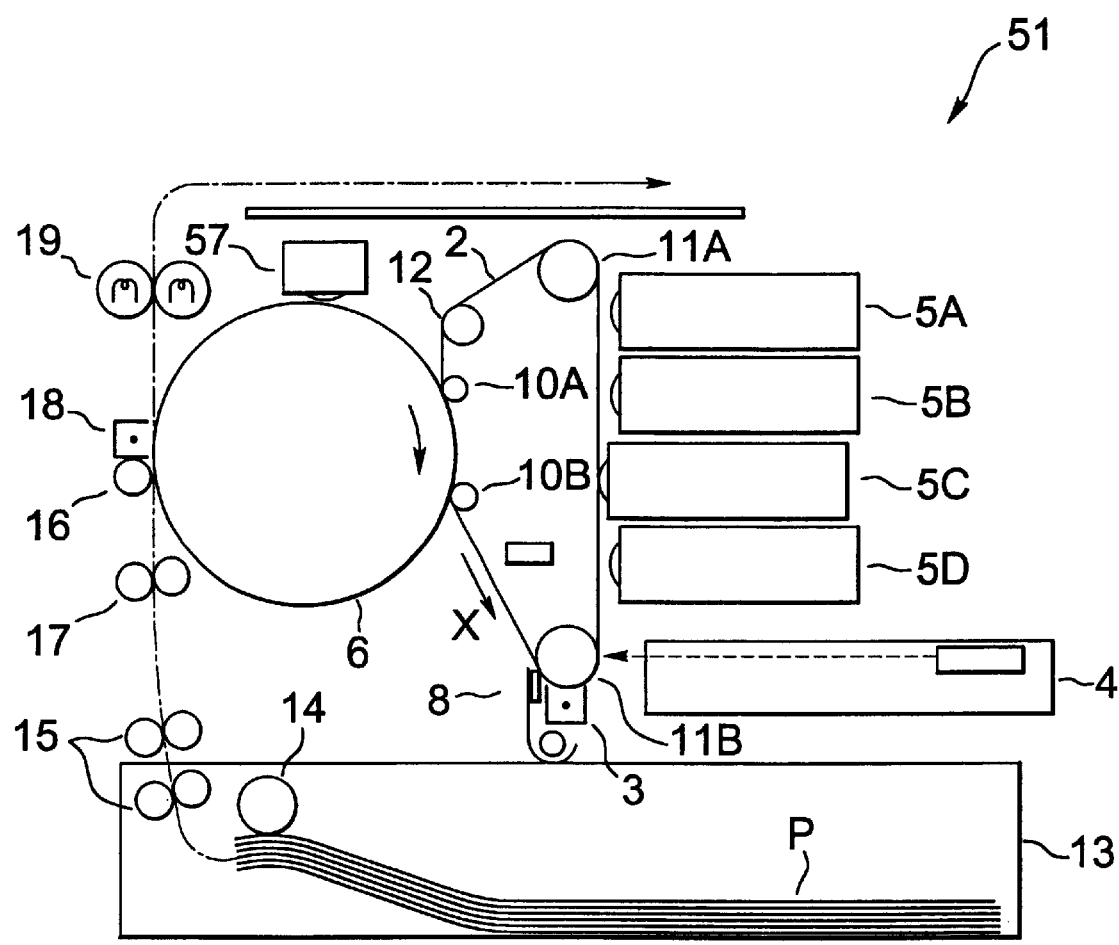
FIG. 5 is a longitudinal sectional view of an image forming apparatus employing a brush system as an intermediate transfer body cleaning device.

Next, the case will be explained where the intermediate transfer drum 6 according to the present invention is applied, in place of the above-described image forming apparatus 1, to an image forming apparatus 51 employing a brush system for applying a bias voltage to a brush to effect cleaning, as a device for cleaning the intermediate transfer drum 6, as shown in FIG. 5.

It is noted that the image forming apparatus 51 has the constitution similar to that of the image forming apparatus 1 except that an intermediate transfer body cleaning device 57 is of a brush system.

is not more than 80° similar to the case of being he image forming apparatus 1, no inside-missing occurs.

TABLE 8 shows the ratio P (=R/r) between outside diameter R of the metal drum 61 and inside diameter r of the rubber belt 62, the value of x=f1×(P−1) when 100% tensile stress of the rubber belt 62 is f1, the permanent elongation (%) in the actual using state, and the situation of occurrence of transfer-missing at the beginning and at the time of use for a long period (after printing of 100,000 sheets in A4 Format).

TABLE 8

| f1 | r(mm) | x | PERMANENT ELONGATION | TRANSFER-MISSING BEGINNING | LONG PERIOD |
|---|---|---|---|---|---|
| 160 | 145 | 25.38 | 5.36 | ○ | ○ |
| 110 | 163 | 3.374 | ** | x | ** |
| 63 | 149 | 8.034 | 10.2 | ○ | x |
| 63 | 150 | 7.56 | 9 | ○ | ○ |
| 90 | 160 | 4.5 | | x | ** |
| 63 | 154 | 5.727 | 8.28 | ○ | ○ |

It is understood that if $x=f1\times(P-1)\geq 5$, and the permanent elongation is not more than 10% in the actual using state, similar to the case of being applied to the image forming apparatus 1, no transfer-missing occurs even at the beginning and at the time of use for a long period.

From the foregoing, if setting up is made in the intermediate transfer drum 6 such that the rubber hardness of the rubber belt 62 is not more than 80°; the ratio between outside diameter R (mm) of the metal drum 61 and inside diameter r (mm) of the rubber belt 62 is P; when 100% tensile stress of the rubber belt 62 is f1 (kgf/cm²), $f1\times(P-1) \geq 5$; and the permanent elongation in the actual using state of the rubber belt 62 is not more than 10%, no slip occurs between the rubber belt 62 and the metal drum 61, and the phenomenon will not occur in which in the formed image, deviation in color occurs, and the rubber belt 62 is twisted and levitated, resulting in defective transfer or irregular transfer.

Moreover, in the intermediate transfer drum 6 according to the present invention, there is not employed the procedure for pouring an adhesive into and between the outer circumferential surface of the metal drum 61 and the inner circumferential surface of the rubber belt 62. Therefore, the yield of the intermediate transfer drum 6 is improved, the mass production is facilitated, and the metal drum 61 can be separated from the rubber belt 62 easily, thus enabling re-using them.

What is claimed is:

1. An intermediate transfer drum for an electrophotographic process molded by putting a rubber belt on a base drum, characterized in that rubber hardness of said rubber belt is set to not more than 80°;

assuming that the ratio between outside diameter R (mm) of said base drum and inside diameter r (mm) of said rubber belt is P, and 100% tensile stress of said rubber belt is f1 (kgf/cm²), then $$f1\times(P-1)\geq 5; \text{ and}$$

permanent elongation in the actual using state of said rubber belt is set to not more than 10%.

2. The intermediate transfer drum according to claim 1, wherein the resistance value is within a range of $10^8$ to $10^{12}$ Ω·cm.

3. An image forming apparatus employing an electrophotographic process comprising a photosensitive body, a charging device for charging said photosensitive body to a fixed potential, an exposing device for irradiating light on said charged photosensitive body to form an electrostatic latent image, a developing device for supplying toner to the electrostatic latent image formed on said photosensitive body to visualize it, an intermediate transfer drum for carrying and supporting a toner image formed on said photosensitive body, and transfer roller for transferring the toner image formed on said intermediate transfer drum to a sheet of paper, characterized in that said intermediate transfer drum being molded by putting a rubber belt on a base drum;

rubber hardness of said rubber belt is set to not more than 80°;

assuming that the ratio between outside diameter R (mm) of said base drum and inside diameter r (mm) of said rubber belt is P, and 100% tensile stress of said rubber belt is f1 (kgf/cm²), then $$f1\times(P-1)\geq 5; \text{ and}$$

permanent elongation in the actual using state of said rubber belt is set to not more than 10%.

4. The image forming apparatus according to claim 3, wherein pressing force of said transfer roller to said intermediate transfer drum is not more than 20 gf/cm.

5. The image forming apparatus according to claim 3, wherein said photosensitive body is belt-like.

* * * * *